United States Patent [19]

Okada et al.

[11] 4,217,241

[45] Aug. 12, 1980

[54] PROCESS FOR THE MICROCAPSULATION OF ORGANOPHOSPHORIC ACID DERIVATIVE-CONTAINING AGRICULTURAL CHEMICALS

[75] Inventors: Yoshio Okada, Tokyo; Yuriko Igarashi, Mitaka; Kozyu Watanabe, Itabashi, all of Japan

[73] Assignee: Kureha Kagaku Kogyo Kabushiki Kaisha, Tokyo, Japan

[21] Appl. No.: 893,822

[22] Filed: Apr. 5, 1978

[30] Foreign Application Priority Data

Apr. 8, 1977 [JP] Japan .................................. 52-39575

[51] Int. Cl.$^2$ ............................................. B01J 13/02
[52] U.S. Cl. ..................................... 252/316; 424/32; 424/33; 424/34; 424/37; 424/219
[58] Field of Search ...................... 252/316; 424/33, 34

[56] References Cited

U.S. PATENT DOCUMENTS

| | | | |
|---|---|---|---|
| 3,551,346 | 12/1970 | Breen et al. | 252/316 |
| 3,576,760 | 4/1971 | Gould et al. | 424/32 X |
| 3,691,090 | 9/1972 | Kitajima et al. | 424/33 X |
| 3,737,337 | 6/1973 | Schnoring et al. | 252/316 X |

FOREIGN PATENT DOCUMENTS

| | | | |
|---|---|---|---|
| 37-12381 | 8/1962 | Japan | 252/316 |
| 37-15761 | 10/1962 | Japan | 252/316 |

*Primary Examiner*—Richard D. Lovering
*Attorney, Agent, or Firm*—Fleit & Jacobson

[57] ABSTRACT

The invention relates to a process for the preparation of microcapsules of organo-phosphoric acid derivative as capsule core. The derivative has a partial mutual solubility with water. The main feature of the invention is the provision of an inner provisional solid capsule shell of a high molecular hydrophobic substance, such as polymethyl methacrylate. This substance is liable to form a shell on each of the droplets by sedimenting under aqueous condition, while it is capable of dissolving into the capsule core substance, when subject to non-aqueous condition which is established after formation of a permanent outer shell on the provisional shell of each capsule. The provisional shell-forming substance is polymethyl methacrylate, polystyrene, polyvinyl chloride or polyvinyl acetate.

2 Claims, No Drawings

PROCESS FOR THE MICROCAPSULATION OF ORGANOPHOSPHORIC ACID DERIVATIVE-CONTAINING AGRICULTURAL CHEMICALS

BACKGROUND OF THE INVENTION

The present invention relates to improvements in and relating to a process for the manufacture of microcapsules of specifically selected agricultural chemicals as of organo-phosphoric acid derivatives adapted for use as agricultural pesticides.

Specifically selected organo-phosphoric acid derivatives such as dimethyl-2,2-dichlorovinyl phosphate (DDVP), dimethyl-1,2-dibromo-2,2-dichloroethyl phosphate are liably subject to hydrolysis and thus rapidly decomposed in natural environment. These compounds are used, therefore, broadly as agricultural pesticides showing least residual phytotoxicity. On the other hand, these compounds represent only short effective term upon application, on account of their high liability to hydrolysis, and thus, they must be applied frequently and repeatedly in practice. In order to avoid this defect, it has been also tried to capsulate these chemicals for the purpose of supressing the hydrolytic liability and to prolong the effective duration term.

For the microcapsulation of organo-phosphoric acid derivatives as the capsule core, the conventional complex coacervation process has hitherto been relied upon. It has been experienced, however, that with such a process as above, the desired microcapsules can not be obtained with high yield.

Taking DDVP as a representative example, the compound shows only about 1% of solubility to water under normal temperature and when it is dissolved in water, the compound is liably subject to hydrolysis, thereby providing phosphoric acid. Therefore, in this case, the solving process in water will continuously progress. Even if the quantitative ratio of DDVP to the aqueous phase is set to 1:10 or so, the capsulation efficiency will be less than 90%.

On the other hand, DDVP dissolves about 10% at normal temperature, the hydrolysis will progress within the capsule upon the formation thereof and the capsulation yield will be about 50% or so. In addition, the preservation of the capsules is highly inferior.

Further, since DDVP is subject to hydrolysis, phosphoric acid is formed and the pH of the aqueous phase will be lowered liably to 3.0 or so by the presence of the formed phosphoric acid, thereby the particle size of the produced microcapsules becoming uneven by virtue of the thus invited unstable and unhomogenized condition of the aqueous emulsion phase. It has been experienced that in prosecution of the complex coacervation process, the range of pH value adapted for the accumulating formation of capsule shell membrane is preferably between 3.9–4.3. Therefore, if the pH value of the aqueous dispersion phase should drop below the above preferable range, adjustment is necessary by addition of alkaline solution. By execution of such alkali addition procedure for pH-concentration adjustment, a neutral salt will develop and adversely affect upon the yield of shell membrane formation by the accumulation of polycationic colloid.

Several prior proposals for providing counter measures against above kind drawbacks have been already published, for instance, in Japanese Patent Publication Nos. Sho-37-12381 and Sho-37-15761, for providing multi-layer microcapsules. According to these proposals, such a measure is adopted during microcapsulation of a hydrophilic substance in the complex coacervation process, a preparatory protecting coating composed of hydrophobic high molecular ethyl cellulose, so as to provide finally a multi-layer microcapsules. However, it has been experienced that when employing such prior proposals for the microcapsulation of organo-phosphoric acid derivatives such as DDVP, many difficulties are met and the desired effect can not practically be attained.

SUMMARY OF THE INVENTION

It is thus the object of the present invention to provide an efficient process for the microcapsulation of organo-phosphoric acid derivative as the capsule core, in an easy and economical way.

In the present invention, and for the microcapsulation of organo-phosphoric acid derivative having a partial, mutual solubility to water, a first and provisional capsule shell is formed and then, a second and permanent capsule shell is formed thereon, so as to provide a double layer capsule structure, of which, however, the first shell is dissolved gradually and automatically dissolved, so as to provide finally a mono-layer capsule shell composed of the said second one only.

As the material for the said first and provisional shell, a high polymer substance having a hydrophobic performance, soluble with the capsule core substance when there is no aqueous component, and yet having a membrane-forming capability under aqueous condition. Although not limited thereto, this provisional shell-forming material may be polymethyl methacrylate, polystyrene, polyvinyl chloride or polyvinyl acetate.

As a preferable mode of the inventive process may be as follows:

To the capsule core-forming organo-phosphoric acid derivative, 100 wt. parts, polymethyl methacrylate, preferably 0.1–10 wt. parts, is added to dissolve therewith, and then, the core substance composition is introduced into a water bath and agitated to divide the core substance into microdroplets coated with polymethyl methacrylate film, so as to provide a distributed and emulsified aqueous phase including these droplets. Then, this phase is subjected to a conventional complex coacervation step for the formation of a second and permanent solid capsule shell. Finally, the thus formed double layer microcapsules are separated from the dispersion phase and dried up. Then, the first and provisional outer capsule shell composed of polymethyl methacrylate is dissolved gradually and automatically with the capsule core substance. In this way, the desired dry microcapsules of mono-layer structure can be effectively provided in an easy and economical way.

It will be, therefore, clearly understood that according to a feature of the present invention, a membrane-forming high polymer substance such as polymethyl methacrylate which is hydrophobic and soluble with the organo-phosphorous derivative constituting the core substance per se at normal temperature and under substantially non-aqueous condition, is added to the non-aqueous organo-phosphoric acid derivative before carrying out the complex coacervation for capsulation. By adopting this predissolving measure, the shell-forming high molecular substance forms a solid film shell on the surface of each of the oily droplets which are distributed and emulsified in the water when the mixed gel solution phase subjected to agitation, diffusion and emulsification, as known per se, during the execution of the complex coacervation process, because it is liable to sediment into a solid from the body of water or the mass of the core-forming substance, if the environment is anhydrous or nearly so. In this way, otherwise possible mutual solution between the core substance per se and the aqueous phase can be effectively prevented.

As a second feature of the present invention, it should be noted that when the provisional double layer microcapsules are taken out from the aqueous dispersion phase and dried up, thus the aqueous content being completely driven off from the composite shell, the provisional inner capsule shell will be redissolved into the core material per se, to disappear, thus leaving the desired mono-layer microcapsules, although the main processing is relied upon the conventional complex coacervation.

The admixing quantity of the provisional shell-forming substance such as polymethyl methacrylate (PMMA) may be about 0.1–10 wt. parts relative to 100 wt. parts, preferably about 1–5 parts, of the core-forming material per se. With lesser amount of the former than about 0.1 wt. parts, difficulty will be encountered in the formation of the provisional shell. On the other hand, when the amount should exceed over about 10 wt. parts, difficulty will be had in the solution of the provisional core-forming substance.

The above solution is added to a conventional complex coacervation mixed solution and agitated for enough distribution and emulsification.

It is effective and preferable to add natural high molecular surfactant such as gelatin to the mixed sol phase, in order to improve the stability of the dispersion.

When the PMMA-component is brought into contact with the aqueous content in the dispersion phase during the emulsifying step, the PMMA is liable to form positively a provisional shell film on each of the divided and distributed oily droplets of the core substance per se, such as DDVP, which represent a highly reduced solubility by contact with the aqueous component, thus the provisional shell film being provided at the interface between the core substance and the water and in the kind of sedimentation. Therefore, the core substance such as DDVP is effectively surrounded by the film shell of PMMA and subjected to almost none of hydrolysis. At this stage, therefore, the droplets take the form of substantially evenly shaped microparticles, each being covered and protected by the film shell.

The complex concervation phase may naturally be of the conventional one. Therefore, the permanent shell-forming substance usable in this process may be polycation colloid, such as natural gelatin, modified gelatin, albumin or the like, while the polyanion colloid may be acacia, gum arabic, carboxy methyl cellulose or the like.

An addition of alkyl naphthalene, such as monoisopropyl naphthalene, diisopropyl naphthalene, to the DDVP-PMMA solution is recommendable, because such high boiling point solvent acts to reduce chance for contact between the DDVP and the water, thereby improving the desired effect of the present invention.

After the dispersion and emulsification in the above sense, the intermediate products are regularly subjected to a second capsulation step by the conventional complex coacervation process, so as to coat the intermediate capsule products further with a second, permanent and outer shell. In the coacervation bath liquid, each of the DDVP-capsules coated provisionally with PMMA-coating are further coated with a polycation colloid film, thus providing each a double layer capsule.

When the double layer capsules are subjected to drying, the provisional PMMA-shell is redissolved into the core substance DDVP, thereby leaving mono-layer capsules of polycation colloid shell which are the desired final products. However, if desired, these final products may further be coated with a proper layer.

The technical reason for use of PMMA or other hydrophobic high molecular substance is to provide a provisional shell around each of the core-forming droplets in a substantially even mode, so as to suppress otherwise possible hydrolysis of the organo-phosphoric acid derivative constituting the capsule core, as met in the capsulation process. Other reason is to prevent excess lowering of pH-concentration in the dispersion system during dispersing and emulsifying period. Still further reason is to capsulate the organo-phosphoric acid derivative which is partially and mutually soluble with water and easily subject to hydrolysis in a highly easy and economical way with a high and stabilized yield, said mono-layer shell being composed of polycation colloid.

By the formation of the inner and provisional shell, the utilizable field of the conventional coacervation process can be substantially enlarged by the present invention. In addition, the effective utility or organo-phosphoric acid derivatives may naturally enlarged to a substantial degree.

DETAILED DESCRIPTION OF THE INVENTION

In the following, several numerical examples will be given for clearer understanding of the present inventive process.

EXAMPLE 1

Polymethyl methacrylate, 0.3 g was dissolved under normal temperature into DDVP. 15 ml. Next, gelatin, 3 g, and gum arabic 3 g, were dissolved in 54 ml of warmed water, 50° C. These both solutions were introduced into a universal homogenizer which was then operated well to disperse and homogenize the mixed liquid charge, until the dispersed oily particles represent 5–10$\mu$ diametrial dimensions.

300 ml of the thus emulsified dispersion was transferred to a beaker and added under agitation with 150 ml of warmed water, 50° C. pH value of this system was in the order of 4.5 which is substantially different from the value to be disclosed in the next following comparative test example 1. The reason was supposed that in the present case, a provisional shell is formed of polymethyl methacrylate which served for reducing otherwise possible hydrolysis of DDVP.

Then, the pH of the system was adjusted to 4.1 with addition of a 5%-acetic acid solution for the execution of a complex coacervation phenomenon. Further, the system solution was cooled to 5° C., added with 3 ml of a 25%-glutaraldehyde. The pH value was adjusted to 6.0 with use of a 1.0%-NaOH solution, so as to execute a capsule-hardening step.

Then, the thus produced microcapsules were filtered off and subjected to a drying step for providing dry capsules.

Upon investigation by cutting a capsule taken out therefrom, it was found that the inner provisional shell of polymethyl methacrylate had disappeared by dissolving into the capsule core substance of DDVP, thereby leaving the permanent outer capsule shell of gelatin. The capsule yield amounted to 91% which was substantially higher than that obtained in the next following comparative test example 1.

COMPARATIVE TEST EXAMPLE 1

Gelatin, 3 g, and gum arabic, 3 g, were dissolved in 54 ml of warmed water, 50° C. Then, this mixed solution was charged in a universal homogenizer, while being added with 15 ml of DDVP, for providing an O/W mode emulsion. The machine was operated until the dispersed DDVP-droplets represented particle diameters of 5–10μ by emulsification.

The emulsifying operation was terminated with these DDVP-particle sizes of 5–10μ, as was referred to above. The pH-value of the suspension system was found 3.1, on account of the hydrolysis to which DDVP was subjected to.

Generally speaking, the optimal pH-value for the coacervation in such gelatin-gum arabic system may amount to 3.9–4.3. Therefore, with the above emulsion attained above represented substantial difficulty in inviting an effective complex coacervation.

Therefore, in order to adjust the pH of the system to the optimal range of 3.9–4.3, a 10%-NaOH solution was added and the capsulation step was carefully progressed. However, the resulted capsule yield amounting only to 45%. Therefore, the present example may be unsatisfactory for the execution of an industrial manufacture.

EXAMPLE 2

In place of polymethyl methacrylate, 0.3 g, polymethyl methacrylate, 1.0 g, was used and other operating conditions were substantially same as in the first Example 1, so as to obtain gelatin-capsules of DDVP. In this case, the capsule yield amounted to 92% which value was substantially higher than the yield obtained in the foregoing comparative test Example 1.

EXAMPLE 3

Using 0.1 g of polymethyl methacrylate, other procedures were substantially followed to the description of the first Example 1. In this case, however, the emulsified dispersion was transferred to a 300 ml-beaker and added with 450 ml of water warmed to 50° C. The pH of the system amounted in this case to about 3.8. However, no pH-adjustment was adopted. Under these conditions, the capsulation was progressed as before, and filtered and dried. In this way, gelatin-capsulated DDVP-microproducts were obtained. The capsule yield amounted to 84% which was, however, substantially higher than that obtained in the foregoing comparative test example.

EXAMPLE 4

6 ml of urea prepolymer solution were added to the capsulating dispersion to produce gelatin capsuled products used in the first Example 1. In this way, gelatin-urea formalin, double layered capsules were obtained. The used urea prepolymer solution had been prepared in such a way that urea, 1 mole, was admixed with 1.2 moles of formalin and then neutralized with aqueous ammonia. The reaction was carried out at 50° C. for 60 minutes. For the formation of urea shells, the pH of the dispersion was adjusted to 3.0 by addition of a 5%-HCl solution. The operating period was for 3 hours at 50° C.

After the formation of urea capsule shells, filtration and drying were executed as before. In this way, double layer capsules were obtained. The capsule yield for DDVP amounted 88%. Therefore, it will be seen that also for the manufacture of gelatine/urea-formalin double layered capsules of DDVP, the formation of the provisional inner shell of polymethyl methacrylate can serve for the improvement of capsule yield.

EXAMPLE 5

Any selected one of polystyrene, polyvinylchloride and polyvinylacetate, 0.5 g, was used at normal temperature in place of 0.3 g of polymethyl methacrylate, relative to 15 ml of DDVP in the first Example 1, and other operating conditions were substantially same as those described therein.

Similar microcapsules were obtained also in this case. The respective yields were as follows:

| provisional shell-forming agent | capsule yield, % |
|---|---|
| polystyrene | 86 |
| polyvinylchloride | 83 |
| polyvinylacetate | 83. |

The embodiments of the invention in which an exclusive property or privilege is claimed are as follows:

1. A process for the production of microcapsules having a permanent outer shell consisting essentially of a material selected from the group consisting of a polycation colloid and a polyanion colloid and having a capsule core substance consisting essentially of an organo-phosphoric acid derivative, said process comprising the steps of:
  (a) adding from about 0.1 to 10 parts by weight of a hydrophobic polymer selected from the group consisting of polymethyl methacrylate, polystyrene, polyvinyl chloride and polyvinyl acetate to 100 parts by weight of said core substance;
  (b) dispersing and emulsifying the resulting core substance-polymer mixture in an aqueous medium to produce microdroplets provisionally covered with a layer composed of said hydrophobic polymer;
  (c) subjecting the microdroplets to the conventional complex coacervation process to form capsules having an outermost solid membrane layer on each of said provisionally coated droplets;
  (d) separating the capsules from the dispersion phase; and
  (e) drying the resultant capsules whereby the provisional, hydrophobic polymer layer dissolves into the core substance to produce mono-layer capsules.

2. The process of claim 1, wherein the organo-phosphoric acid derivative is selected from the group consisting of dimethyl-2, 2-dichlorovinyl phosphate and dimethyl-1, 2-dibromo-2, 2-dichloroethyl phosphate.

* * * * *